United States Patent
Mollerus (10) Patent No.: US 8,150,514 B2
(45) Date of Patent: Apr. 3, 2012

(54) SPECTRAL SELECTION OF OPERATING MODE IN AN IMPLANTABLE STIMULATOR DEVICE

(76) Inventor: Michael E. Mollerus, Duluth, MN (US)

( * ) Notice: Subject to any disclaimer, the term of this patent is extended or adjusted under 35 U.S.C. 154(b) by 81 days.

(21) Appl. No.: 12/583,482

(22) Filed: Aug. 21, 2009

(65) Prior Publication Data

US 2010/0049267 A1 Feb. 25, 2010

Related U.S. Application Data

(60) Provisional application No. 61/189,835, filed on Aug. 22, 2008.

(51) Int. Cl.
*A61N 1/362* (2006.01)
(52) U.S. Cl. .......... 607/14; 600/515; 600/518
(58) Field of Classification Search .......... None
See application file for complete search history.

(56) References Cited

U.S. PATENT DOCUMENTS

| | | | |
|---|---|---|---|
| 5,778,881 A | 7/1998 | Sun et al. | |
| 6,393,316 B1 | 5/2002 | Gillberg et al. | |
| 6,400,986 B1* | 6/2002 | Sun et al. ................ | 607/14 |
| 6,597,943 B2* | 7/2003 | Taha et al. ................ | 600/515 |
| 7,031,770 B2 | 4/2006 | Collins et al. | |
| 7,123,954 B2* | 10/2006 | Narayan et al. ........... | 600/518 |
| 2002/0120206 A1* | 8/2002 | Taha et al. ............... | 600/515 |
| 2006/0111747 A1 | 5/2006 | Cazares et al. | |
| 2009/0131996 A1* | 5/2009 | Li ............................ | 607/4 |

OTHER PUBLICATIONS

The International Search Report dated Mar. 19, 2010.

* cited by examiner

*Primary Examiner* — Kennedy Schaetzle
(74) *Attorney, Agent, or Firm* — Beck & Tysver PLLC (57) ABSTRACT

A spectral fingerprint technique is disclosed that allows an ICD to eliminate unnecessary shocks to the heart.

11 Claims, 13 Drawing Sheets

| | VF | BR | ARTIFACT |
|---|---|---|---|
| ER | 0.9090 (0.8180, 0.9590) | 0.3370 (0.2480, 0.4100) p < 0.00001 | 0.2650 (0.1885, 0.3700) p < 0.00001 |
| DF (Hz) | 4.5 (4.5, 5.0) | 2.4 (2.0, 4.0) p < 0.00001 | 3.0 (2.5, 6.3) p = 0.014 |
| RMSR | 0.9990 (0.9910, 1.0000) | 0.5310 (0.3450, 0.6030) p < 0.00001 | 0.4900 (0.2915, 0.6310) p < 0.00001 |

Fig. 14

| | CUTOFF (SENSITIVITY, SPECIFICITY) | ROC AUC (95% CI) | KENDALL'S t (95% CI) |
|---|---|---|---|
| PSD | > 0.893 (100%, 98%) | 0.992 (0.962 TO 0.999) | NA |
| HAAR | > 0.850 (95%, 88%) | 0.953 (0.909 TO 0.980) (p = 0.06) | -0.05 (-0.27 TO 0.14) (p = 0.58) |
| DAUBECHIES | > 0.831 (97%, 94%) | 0.974 (0.937 TO 0.992) (p = 0.23) | 0.15 (-0.06 TO 0.36) (p = 0.10) |
| SYMLET | > 0.926 (100%, 98%) | 0.995 (0.969 TO 0.999) (p = 0.62) | 0.51 (0.34 TO 0.67) (p < 0.0001) |

Fig. 15

| | CUTOFF (SENSITIVITY, SPECIFICITY) | ROC AUC (95% CI) | KENDALL'S t (95% CI) |
|---|---|---|---|
| PSD | > 0.529 (100%, 99%) | 0.991 (0.961 TO 0.999) | NA |
| HAAR | > 0.561 (95%, 81%) | 0.950 (0.905 TO 0.978) ($p = 0.05$) | -0.05 (-0.13 TO 0.27) ($p = 0.58$) |
| DAUBECHIES | > 0.553 (100%, 94%) | 0.986 (0.954 TO 0.998) ($p = 0.68$) | 0.23 (0.03 TO 0.40) ($p = 0.01$) |
| SYMLET | > 0.700 (95%, 98%) | 0.988 (0.957 TO 0.998) ($p = 0.79$) | 0.59 (0.44 TO 0.71) ($p < 0.0001$) |

SPECTRAL SELECTION OF OPERATING MODE IN AN IMPLANTABLE STIMULATOR DEVICE

CROSS-REFERENCE TO RELATED CASES

The present case is the utility conversion from U.S. Provisional Application 61/189,835 filed Aug. 22, 2008 entitled "Use of Spectral Analysis to Improve the Performance of Implanted Medical Devices". This application claims the benefit of the provisional application and incorporates it by reference in its entirety.

FIELD OF THE INVENTION

The present invention relates generally to implanted medical devices such as pacemakers and implantable cardioverter-defibrillators (ICD). More specifically, the invention is illustrated in the context of a single chamber ICD of the type that also provides bradycardia pacing. The specification describes and teaches a method of improving the ability of an ICD to distinguish normal heart rhythms from noise or other artifacts sensed by the device, as well as rapid ventricular tachyarrhythmia from noise or other artifacts sensed by the device or from supraventricular tachyarrhythmia.

BACKGROUND OF THE INVENTION

An implantable cardioverter-defibrillator (ICD) is a member of a class of devices called implantable medical devices (IMD). Conventional pacemakers and ICDs as well as other IMDs use electronic sense amplifiers to detect the electrical signals arising from spontaneous or inherent electrical activation in the heart. Modern single chamber ICDs have a dedicated lead system, usually but not always transvenous, coupled to the right ventricle of the heart. The typical lead system will have a defibrillation coil electrode inside the right ventricle, and either another coil, usually in the superior vena cava (SVC) and/or the generator case serves as the other pole in the shocking circuit. The typical lead will also have a bipolar pair of electrodes at the tip of the lead system near the endocardium of the right heart. This pair of electrodes includes a distal tip electrode and a more proximal ring electrode or distal coil. It is this pair of electrodes that is usually connected to a sense amplifier in the ICD. The electromyographic waveform arises in part from the passage of a depolarization wavefront event or R-wave, past the electrode site. The band pass and gain characteristics of the sense amplifier is "tuned" to discriminate this relatively large (voltage) physiologic signal (EMG) from myopotentials and other electrical noise signals that also may be picked up by the electrode or intercepted by the implanted lead system.

A significant problem occurs when there is enough energy presented to the sense amplifier to "trick" the sense amplifier into mistaking noise for a cardiac signal. External sources of noise include both ambient electrical noise such as electromagnetic interference (EMI) as well as artifact from compromises in lead integrity. This external noise or artifact can lead to significant clinical problems. Since the relative timing of one detected cardiac event to the next detected cardiac event is used for rhythm analysis and the invocation of therapy, such noise can inhibit the proper operation of the IMD. For example, in the time domain, two or more R-waves may occur close together in time indicating that a tachycardia or fibrillation may exist. The device may be programmed to intervene and aggressively treat the heart if several rapid beats are detected in a row. In this example, the detection of noise and its incorrect interpretation as a sequence of several fast R-waves may result in treatment where none is required. Or the detection of noise may mask the detection of the absence of normal underlying ventricular rhythm and therefore pacing therapy will be withheld when in fact it is required. Both false positives and false negatives may be harmful.

Another significant problem arises from the inability of the ICD to distinguish ventricular tachycardia—a heart rhythm that originates from the ventricles—from supraventricular tachycardia such as atrial fibrillation—a heart rhythm that originates from the atria. Rapidly conducted signal from the atria to the ventricles may be interpreted inappropriately as ventricular tachycardia and so inappropriate shock therapy may be delivered. In this instance, both supraventricular tachycardia and ventricular tachycardia may have rates that exceed a time domain rate cutoff value.

It is recognized that efforts need to be devoted to improving the ability of implanted devices to detect and correctly interpret heart rhythms.

SUMMARY OF THE INVENTION

The spectral finger print techniques disclosed herein may be applied to implantable medical devices including single chamber, dual chamber, and biventricular pacemakers and single chamber, dual chamber and biventricular implantable cardioverter defibrillators (ICD). In the interest of clarity the invention is disclosed in the context of a single chamber ICD that also provides ventricular bradycardia pacing. The claims should not be limited to the single chamber embodiment which is intended to be illustrative and not limiting. In operation the device performs an analysis of the waveform detected from the ventricular electrode sites and classes the signal as ventricular fibrillation (VF), ventricular tachycardia (VT), external noise or supraventricular tachycardia. The analysis is used to guide therapy in parallel with and in conjunction with conventional time domain rhythm analysis.

In operation, the ICD or pacemaker uses conventional signal sensing and rhythm analysis to determine if a bradycardia arrhythmia is present. This conventional information is used to guide the bradycardia therapy. However if a high ventricular rate is detected the hardware and software of the invention are activated unless they are already activated and another layer of decision-making is invoked.

More specifically, in the presence of a high detected rate the device may activate additional computational power and use frequency domain transformation such as Fourier transforms or wavelet packet analysis on selected and digitized segments of the buffered raw signals from the ventricular electrodes to distinguish supraventricular tachycardia (SVT), atrial fibrillation (AF) from VT and to distinguish VF from EMI, lead artifact and other noise.

In use, the ICD will cancel an otherwise scheduled shock unless the detected rhythm is confirmed as an episode of VF or VT. If the ICD confirms the presence of a supraventricular tachycardia instead of ventricular tachycardia, shock or anti-tachycardia pacing (ATP) may be withheld. In the presence of EMI or other noise, the device may enter a "safe" pacing mode in select pacemaker-dependent patients; a mode that may be selected by the prescribing provider.

DESCRIPTION OF THE INVENTION

Figure 1:
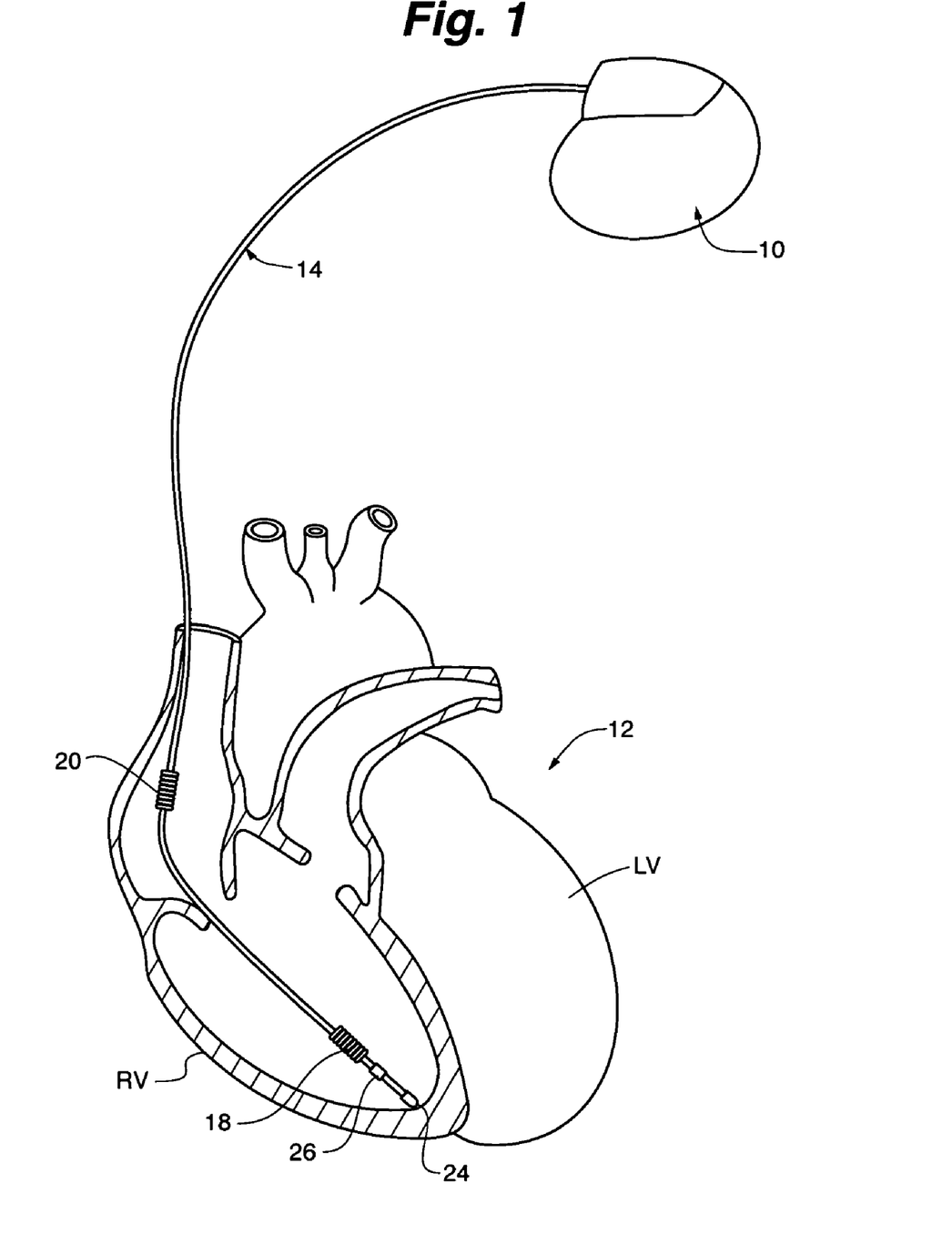
FIG. 1 is a schematic diagram of a representative IMD system.

FIG. 1 shows the context of the invention. The system is totally implanted with the ICD 10 coupled to the patient's heart 12 through a lead system 14. The lead system 14 includes a distal defibrillation coil 18 near the right ventricular myocardium, frequently the right ventricular apex, and usually a proximal coil 22 in the superior vena cava (SVC). Conventional bipolar pacing and sensing leads include tip electrode 24 and ring electrode 26 on the lead, though sometimes the bipolar pair may consist of the distal tip electrode 24 and distal coil 18.

The ICD 10 provides conventional bradycardia pacing in the event of inadequate heart rate. At high rates the ICD may intervene and provide a shock to the heart to treat the arrhythmia as is customary. However in the presence of a high detected rate an additional layer of analysis is performed to improve therapy and avoid unnecessary shock therapy which may be painful.

Figure 2:
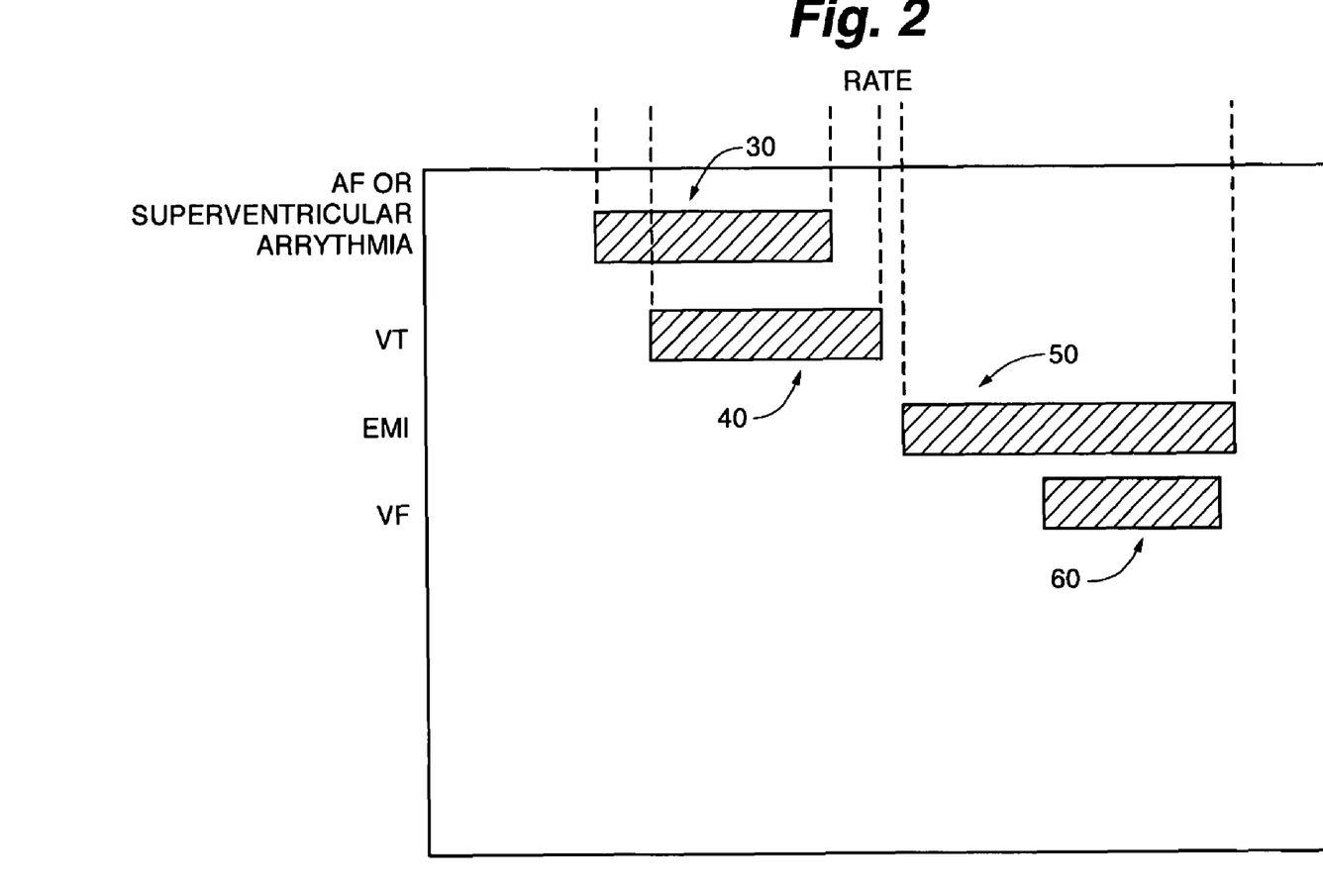
FIG. 2 is a chart.

FIG. 2 is a chart depicting the problem set forth in the background section. As seen in the figure, SVT atrial artifact or AF 30 and ventricular tachyarrhythmia VT 40 may share the same rate. In a similar fashion, electromagnetic interference or EMI 50, and other noise may overlap the ventricular fibrillation VF 60 rate as well. Rate only discrimination techniques frequently are unable to distinguish VF from noise or artifact and VT from supraventricular tachycardia.

Figure 3:
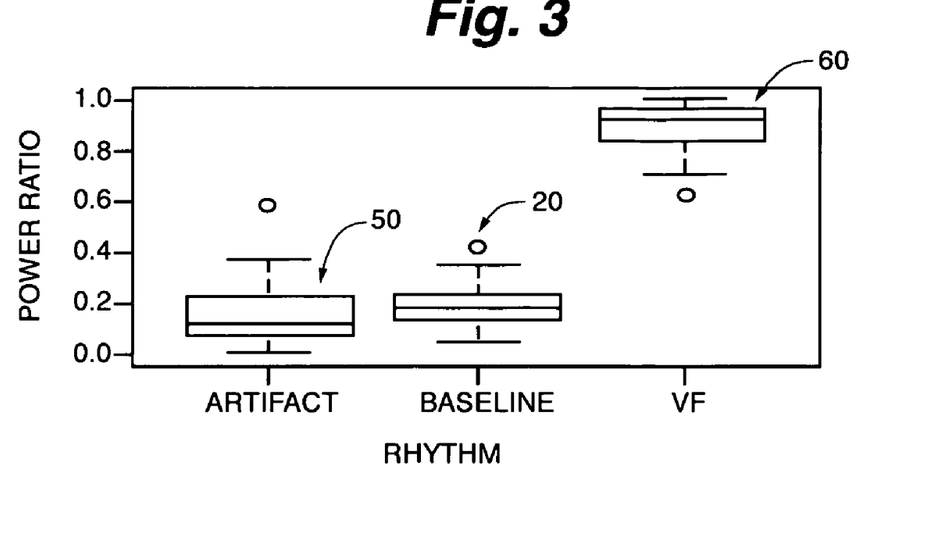
FIG. 3 is a graph derived from test data.
Figure 4:
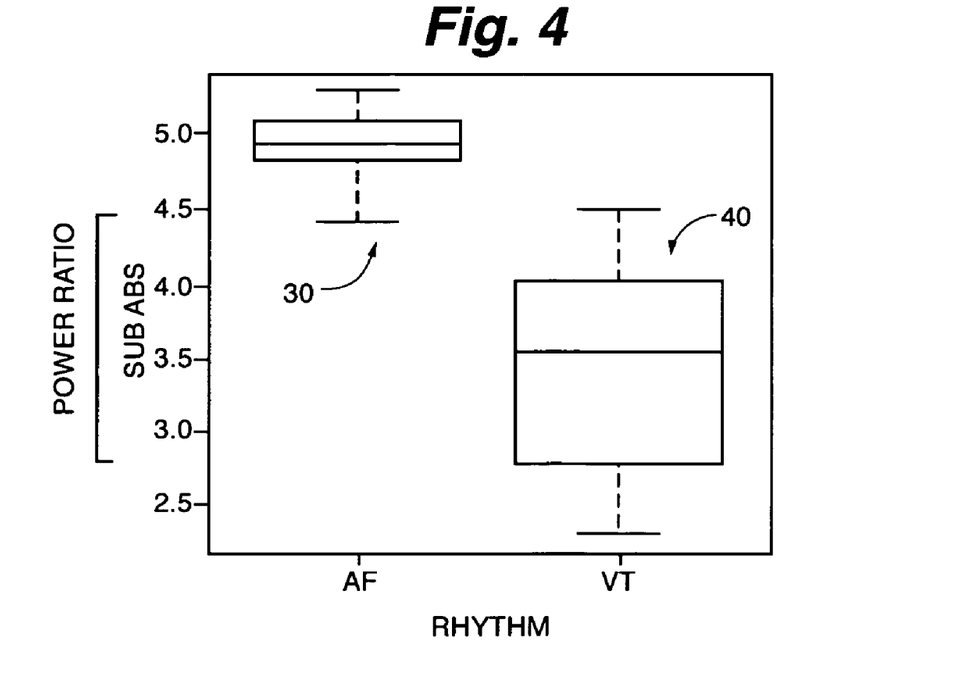
FIG. 4 is a graph derived from test data.

FIG. 3 and FIG. 4 should be considered together. FIG. 3 represents actual testing done with human data sets collected from 32 patients receiving ICD therapy for ventricular fibrillation (VF) at time of routine defibrillation threshold testing. Sixty-four induced VF, and 64 baseline rhythm and 48 artifact events (NONVF) were analyzed. Artifact events included set-screw and cautery artifact. VF was induced using low energy T-wave shocks. The output of the spectral fingerprint technique shows excellent separation of the VF signature with an energy ratio of approximately 0.917 compared with the energy ratio of EMI/Artifact of about 0.110 (p<0.0001). FIG. 4 represents testing done on 14 atrial fibrillation and 9 ventricular tachycardia events retrieved from clinical episodes. Analysis was performed using Matlab software with the Signal Processing Package. Shannon entropy between 2-20 Hz was calculated to compare the two data sets. In a similar fashion the spectral fingerprint technique shows excellent separation of AF 30 from VT 40 with using the Shannon entropy of the frequency transformation between 2-20 Hz. The entropy of Atrial Fibrillation was 4.929 (4.796,5.073) bits while the entropy of Ventricular Tachycardia was 3.520 (2.760, 4.007) bits (p=0.004). The data sets used for FIG. 4 are not as extensive as the data used for the experiments presented in FIG. 3.

Figure 14:
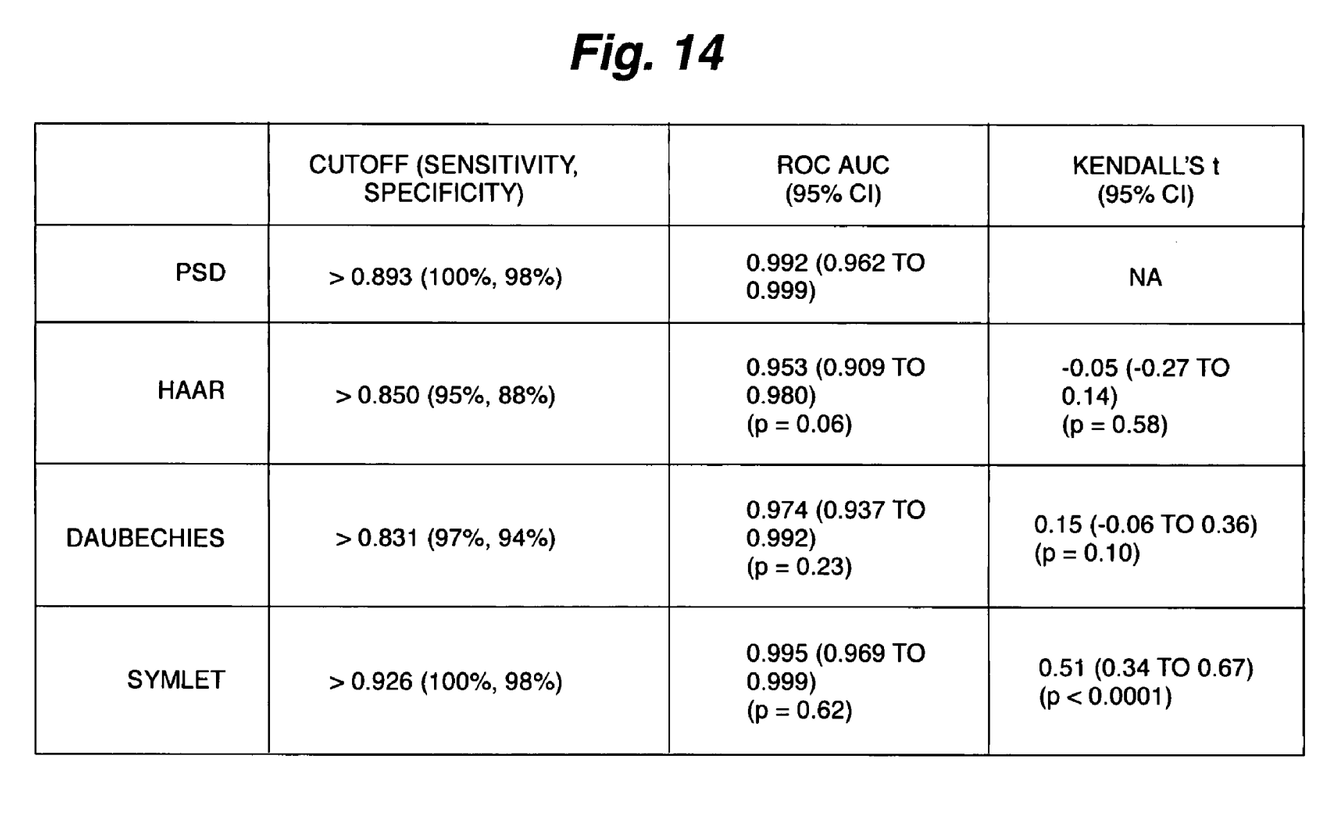
FIG. 14 is a table summarizing results.
Figure 15:
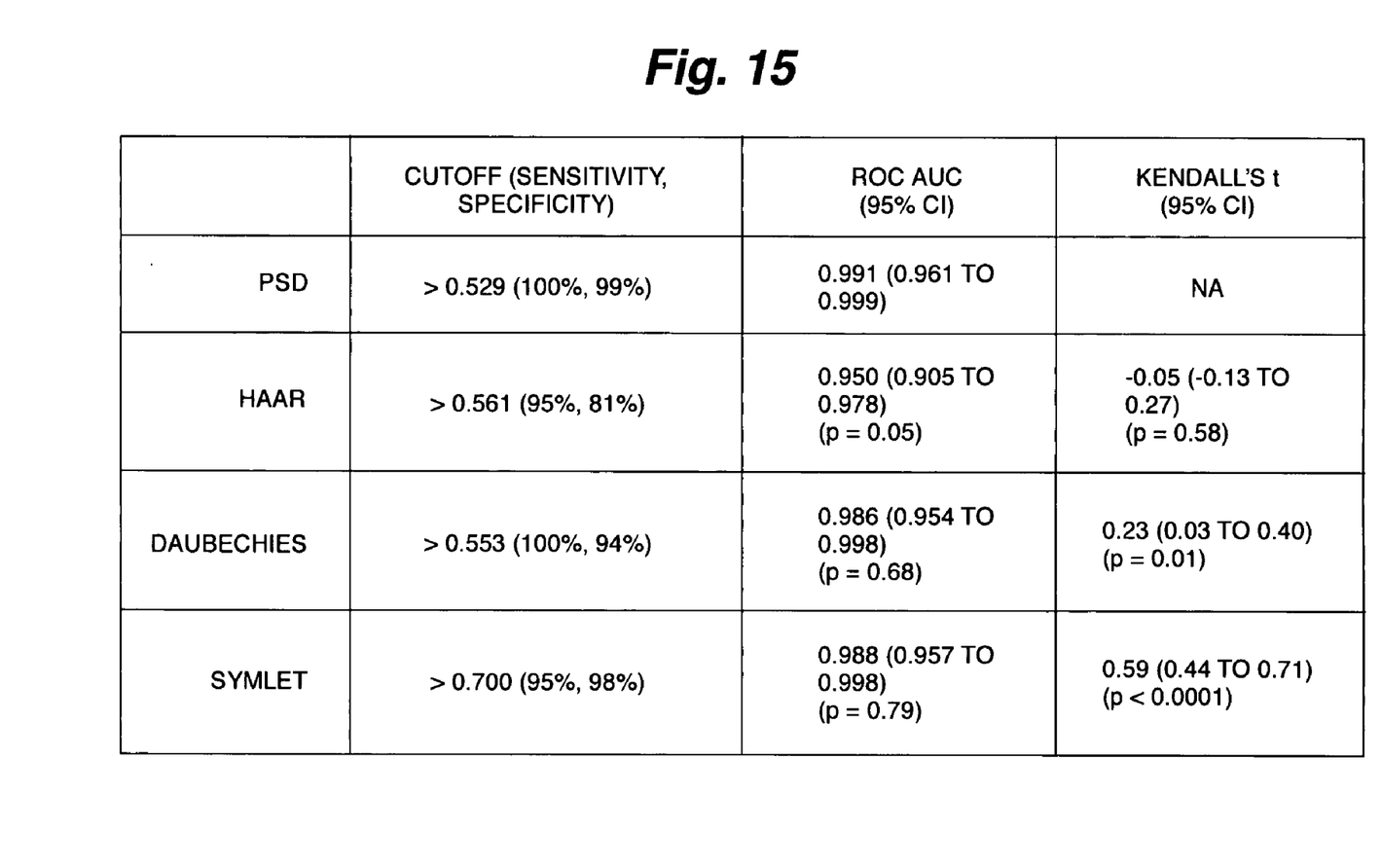
FIG. 15 is a table summarizing results.

FIG. 3 and FIG. 4 represent the output experimental studies carried out on prerecorded waveform data manipulated using a Matlab software package on a desk top computer. Each of FIG. 3 and FIG. 4 show the ability to partition the input waveform into electrical noise artifact 50 (FIG. 3) or atrial fibrillation or SVT artifact 30 (FIG. 4) from the desired signal of ventricular fibrillation 60 (FIG. 3) and ventricular tachycardia 40 (FIG. 4), and to distinguish these spectral fingerprints from the baseline rhythm 20 (FIG. 3). The data is shown in graphic form in FIG. 3 and FIG. 4 and tabular form on FIG. 13, FIG. 14 and FIG. 15.

Figure 13:
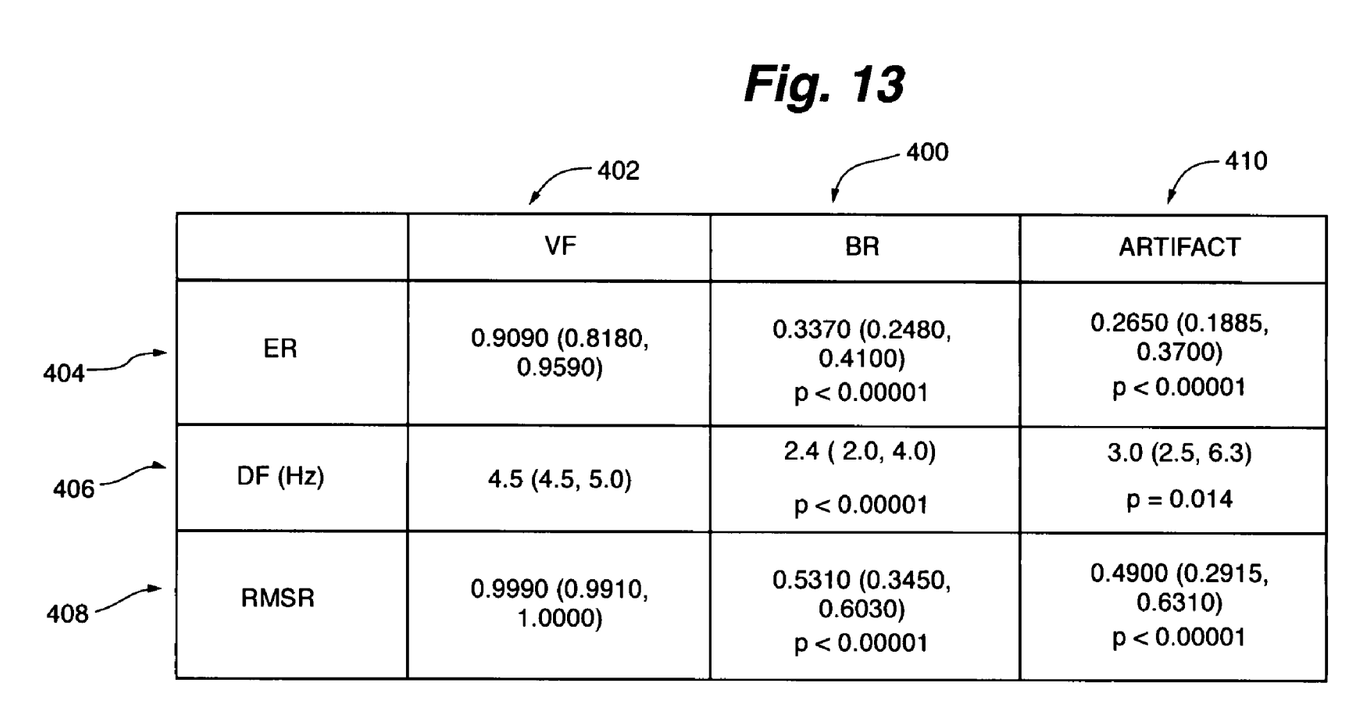
FIG. 13 is a table summarizing results.

FIG. 13 represents data in tabular form from an analysis of 31 patients. Sixty VF and 104 baseline rhythm and artifact (NONVF) events were analyzed, and energy (power) ratios and root mean square ratios were calculated from spectral transformations using both power spectral density (periodogram) and wavelet techniques. Baseline rhythm BR 400 and artifact 410 are compared to ventricular fibrillation VF 402. Energy rations (power rations) and root mean square ratios are compared on lines 404 and 408. Line 406 represents the dominant frequency found in BR 400, artifact 410, and VF 402. The data presented in the figures compares the spectral fingerprint identification of ventricular fibrillation and ventricular tachycardia with other events that were misinterpreted by the devices as either ventricular fibrillation or ventricular tachycardia and are contrasted using either a Welch Two Sample t-test for normally distributed data or the Wilcoxon Rank Sum test for nonparametric data. The figures show dramatic separation between the noise and the signal using the spectral fingerprint technique.

FIG. 3 depicts the ability of the spectral fingerprint techniques of the invention to distinguish ventricular fibrillation from external and extraneous noise using the Welch periodogram described in detail herein. In the figure the technique allows VF 60 to be separated from noise artifacts 50.

FIG. 4 depicts the ability of the spectral fingerprint techniques invention to distinguish ventricular tachycardia from atrial fibrillation 30 noise using the periodogram and described in detail herein. In the figure the technique allows VT to be separated from AF 30 noise.

Figure 5:
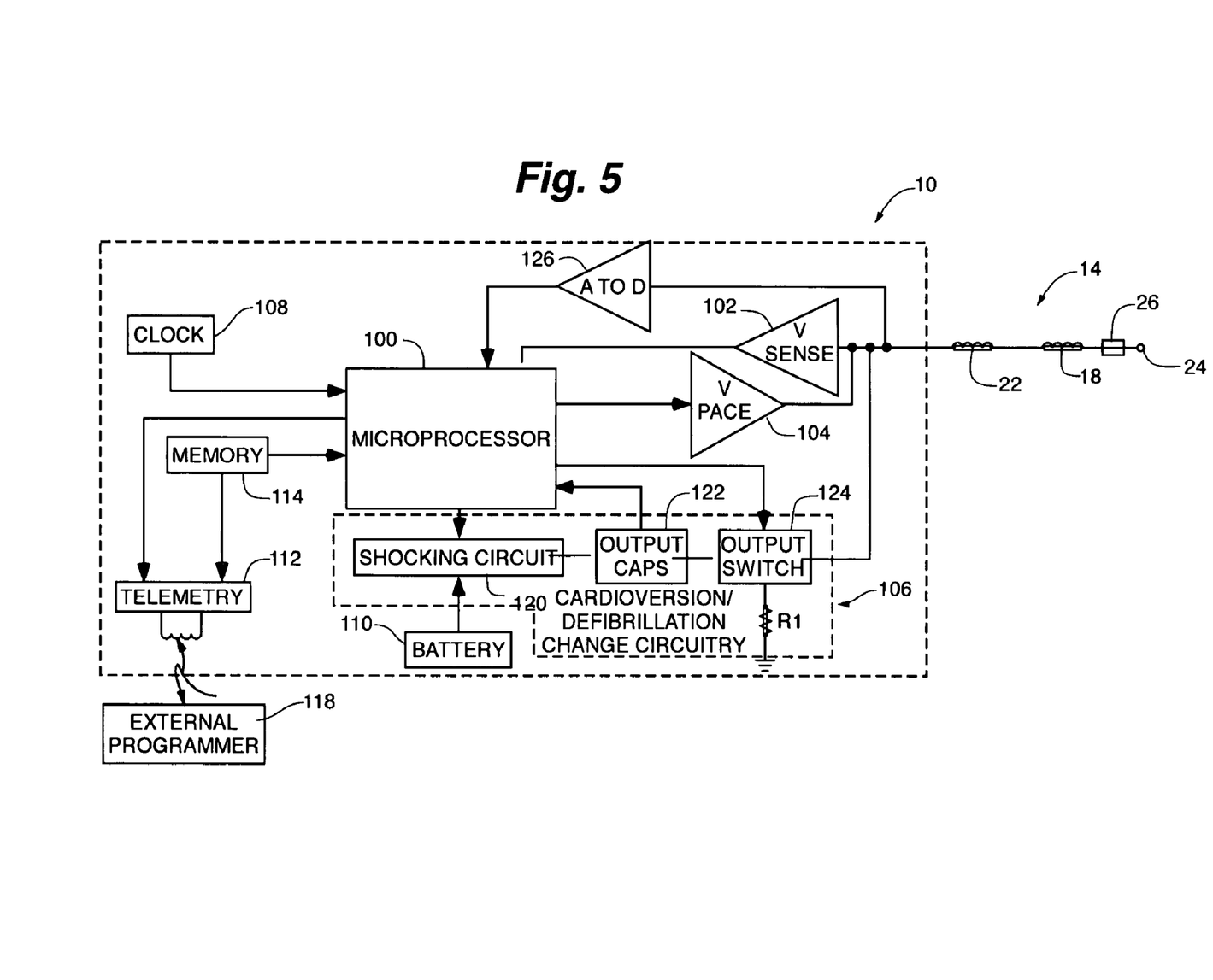
FIG. 5 is a schematic of a hardware implementation of an ICD.

FIG. 5 sets forth one exemplary and illustrative single channel implementation for carrying out the invention. The ICD 10 is coupled to a lead system 14. Within the device "can" there is a battery 110 to power various electronic modules. The microprocessor module 100 operates under the control of a stored program or "software" read from memory 114. This software implements the pacing and defibrillation algorithms that control the acquisition of signals and delivery of stimuli to the heart. Parameters and operating modalities are selected by the physician and they are entered into the memory 114 via a remote programmer 118 via a telemetry module 112. In operation the sense amplifier 102 and pacing pulse generator 104 carry out bradycardia pacing at low sensed rate. If the sensed rate is high the output capacitor array 122 begins to charge and the device enters a spectral fingerprint analysis mode. In this mode the computational load of the microprocessor 100 is increased and clock 108 rates or other techniques to increase processing power may be invoked to rapidly assess the quality of the sensed signal. In this hardware implementation raw signal waveforms are digitized and accumulated for a short time. Dedicated AtoD module 126 hardware is shown to partially carry out this function. The software processing of the accumulated signal from the lead system 14 is carried out in the microprocessor 100. Alternative architectures are possible within the scope of the invention. As described in connection with FIG. 6 in more detail, the device 10 provides rhythm support at low programmed sensed rates. Upon the detection of a rate above a rate threshold the device acquires and signals and performs the spectral analysis. If the spectral fingerprint confirms a treatable arrhythmia then the device discharges the capacitors though the defibrillation electrodes 22 and 18 to arrest the arrhythmia. If the spectral fingerprint analysis indicates that the signal is neither ventricular tachycardia or ventricular fibrillation, then typically the device will cancel the shock and in turn may enter a safe pacing mode such as VOO at a modest rate (60-80 bpm) in pacemaker-dependent patients until the abnormal signal ceases.

Figure 6:
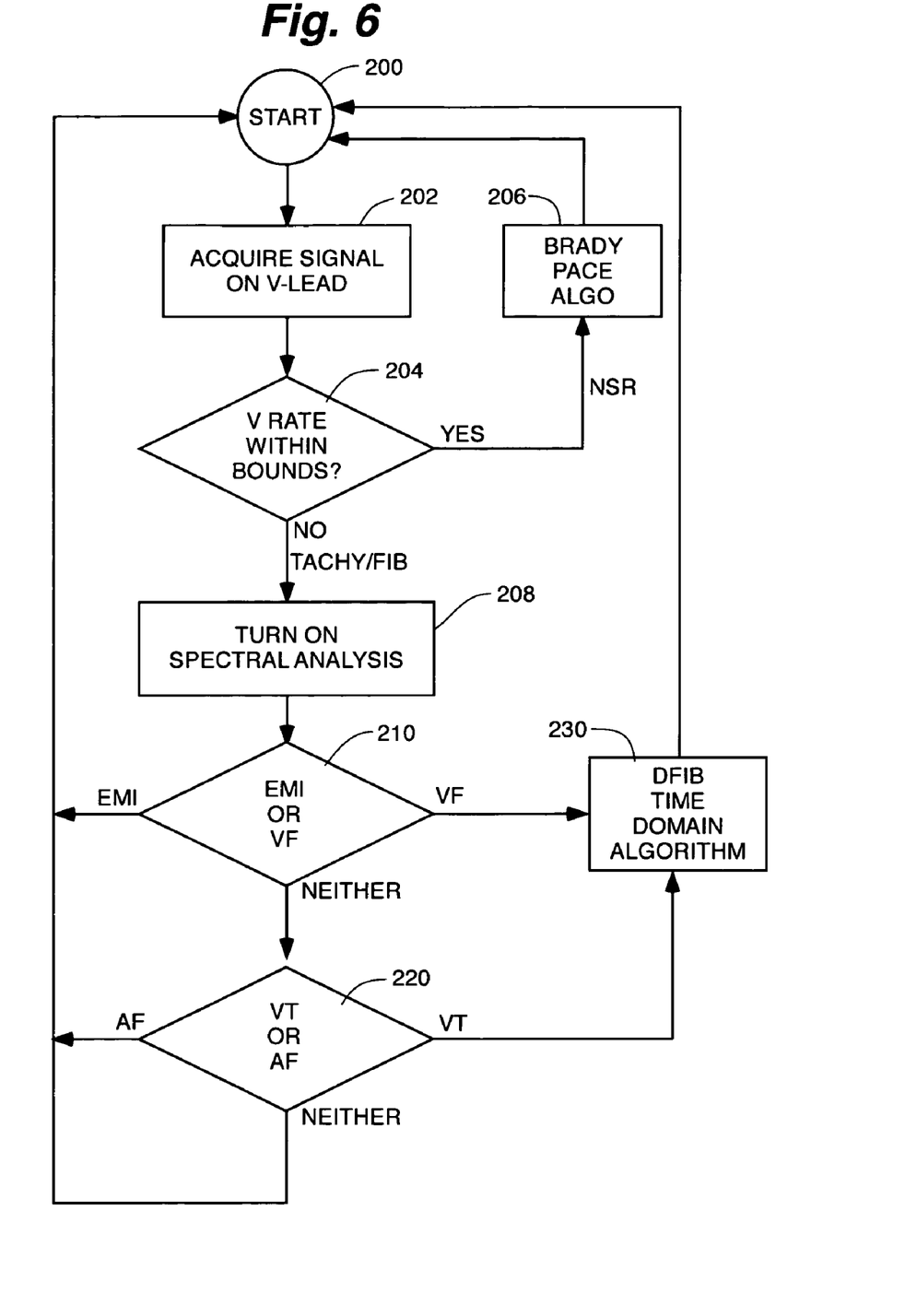
FIG. 6 is a flow chart showing the ICD operation.
Figure 7:
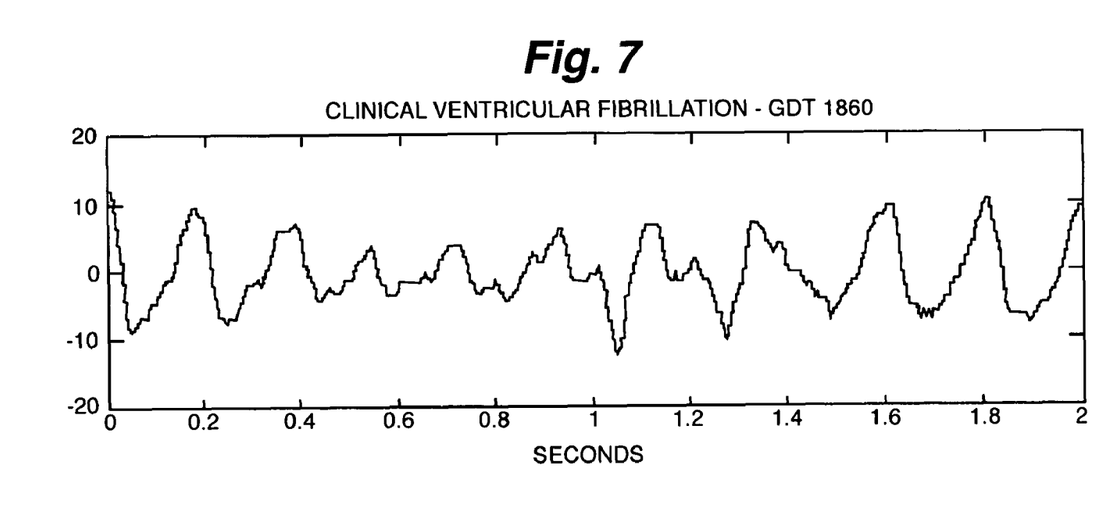
FIG. 7 is a pictorial representation of the VF waveform.
Figure 8:
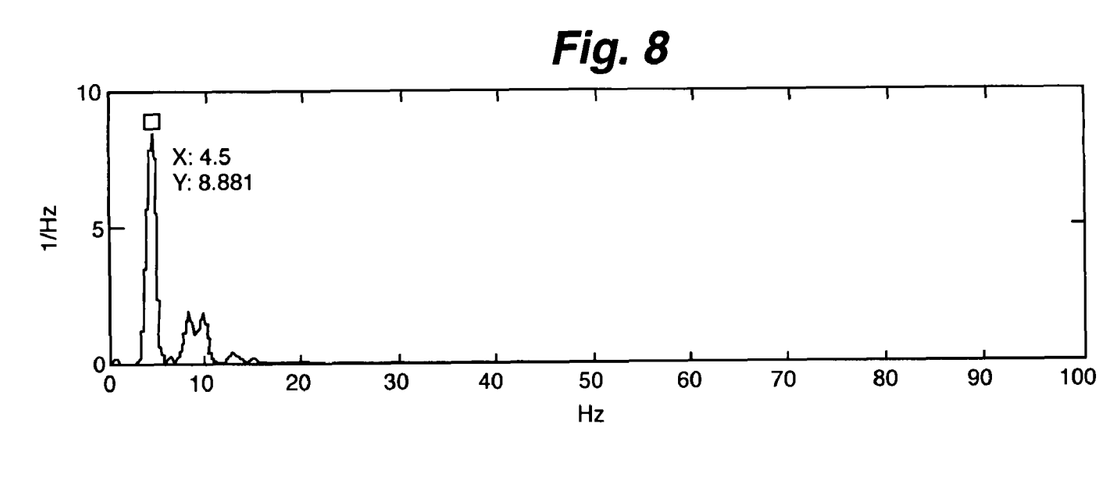
FIG. 8 is a pictorial representation of the first three harmonics of the FIG. 7 VF waveform in the frequency domain.
Figure 9:
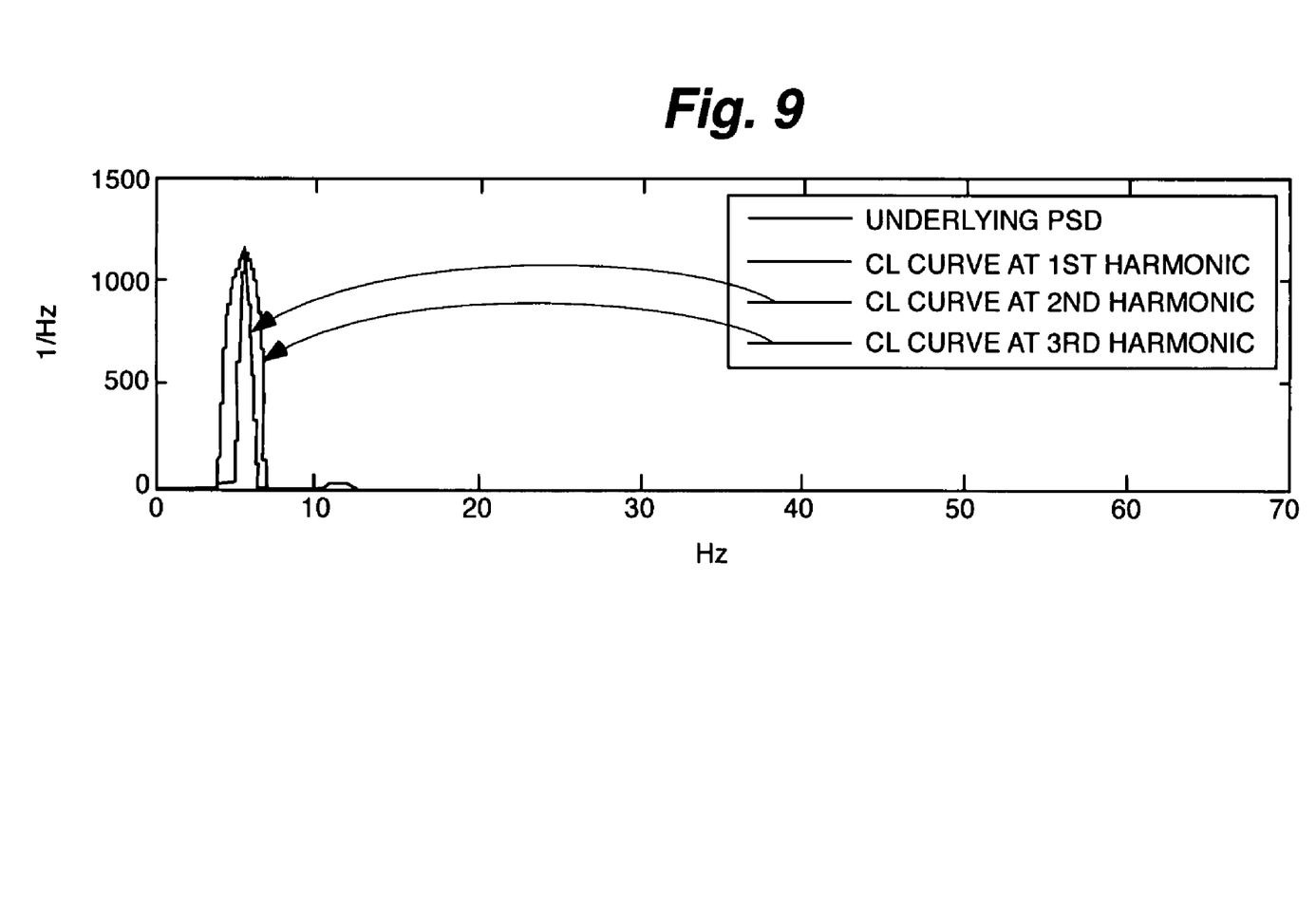
FIG. 9 is a pictorial representation of the Cauchy-Lorentz curve fitting the first three harmonics of the power spectral density calculation.

FIG. 6 is a high level flowchart showing the operation of an ICD of the type shown in FIG. 5 carrying out the invention. By way of overview, the processes 200 though 206 act as a conventional bradycardia pacemaker providing support for rate insufficiency in this implementation. However if a high rate is sensed the spectral analysis system is activated at process 208 and the input waveform is tested for electromagnetic interference noise or artifact such as EMI or supraventricular rhythms such as AF. If these waveforms are determined to be EMI/artifact or supraventricular tachycardia, the device does not intervene with a high energy shock. However if the VT or VF episode is confirmed by spectral analysis, the device generates a shock according to programmed parameters in process 230. In essence by transforming the signal to the frequency domain and measuring characteristics of the signal including power of the first three harmonics or Shannon entropy, the device can declare the presence of noise/artifact or supraventricular tachycardia and the absence of a ventricular arrhythmia and respond by canceling a shock therapy if a ventricular arrhythmia is declared based upon the time domain rate threshold.

In more detail the method begins with process 200. In this process the device is operating to observe the heart rhythm and operates in accordance with parameter values loaded by the physician. In process 202 electrical signals are detected on the implanted leads by sense amplifier. If sufficient energy exists in the pass band of the sense amplifier, the device declares a depolarization event to the logic in process 204.

In process 204 the ventricular rate is evaluated to see if it lies between programmed bounds. For example if the detect rate is within the bounds of normal heart activity between say 60 bpm and 120 bpm the device will enter process 206 where the decision to supply or withhold bradycardia pacing is made according to the selected pacing modality. If the device paces an appropriate stimulus is provided on the ventricle lead 14. If stimuli are withheld then the device is quiescent. In either event the device reenters the start process waiting for another sensed event.

If the ventricular rate is high and therefore potentially lethal the device enters process 208 where the spectral analysis processes are activated. It is expected that the processing power to carry out the spectral analysis described herein will require substantial current drain on the battery and that activation of the these processes only when a high rate is detected. However, it is conceivable that the spectral analysis process may be on all the time.

By way of overview the high detected ventricular rate that activates the spectral analysis processes needs to be either confirmed in process 210 and or process 220 as pathologic and used to treat the patient or else attributed to noise or other spurious signals or artifacts. In the event of noise or spurious signal, the high rate will not be used to invoke a therapy. The device will return to or default to its brady pacing modalities in process 206. However if the patient is pacemaker dependent, it may be preferable to default to a VOO or other appropriate pacing mode. This behavior can programmed by the prescribing provider and tailored to the patients specific needs. Turning to process 210 in more detail, the spectral fingerprint process undertakes a frequency transformation using techniques such as wavelet analysis or Fourier transformation of a segment of data and determines if the incoming signal is VF or EMI or neither. In general the process will collect data from the nearfield ring 26 and tip 24 electrodes or from farfield electrograms such as tip 24 and generator 10 and digitize it with an A-to-D converter 126 (FIG. 5). Process 210 evaluates the signal on the ventricular lead which is digitized. A brief period of signal, for example 2 seconds, may be acquired and optionally trend line determined to remove signal drift.

This signal is then subjected to spectral analysis. Spectral analysis may be done by microprocessor 100 under the control of software. It should also be noted that Digital Signal Processors (DSP) are now available that can carry out he computations in an efficient manner. The utility of the invention does not depend on the particular implementation. As set forth in the following description both energy ratio ER calculation using the ratio of energy under the first three harmonics of the signal are compared with the entire spectrum and an alternative root mean square ratio RMSR was calculated using a ratio of the RMS of the first three harmonics to the entire spectrum were compared with each other. These are both alternative ways of describing the spectral characteristics of the signal. Data suggests that either metric is usable for the spectral fingerprint for VT confirmation. In general the applicants favor the technique with the least computation requirements.

Figure 10:
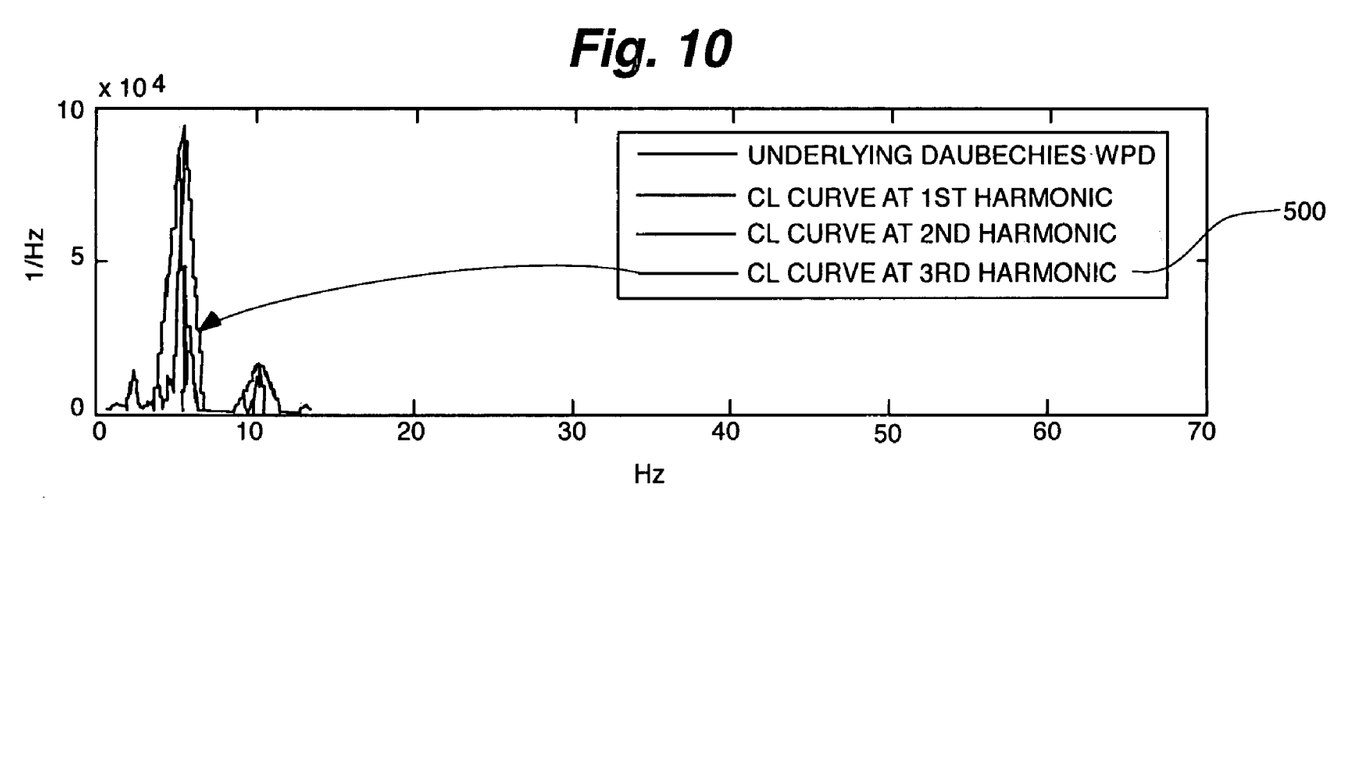
FIG. 10 is a pictorial representation of the Cauchy-Lorentz curve fitting the first three harmonics of the Daubechies wavelet packet decomposition calculation.
Figure 11:
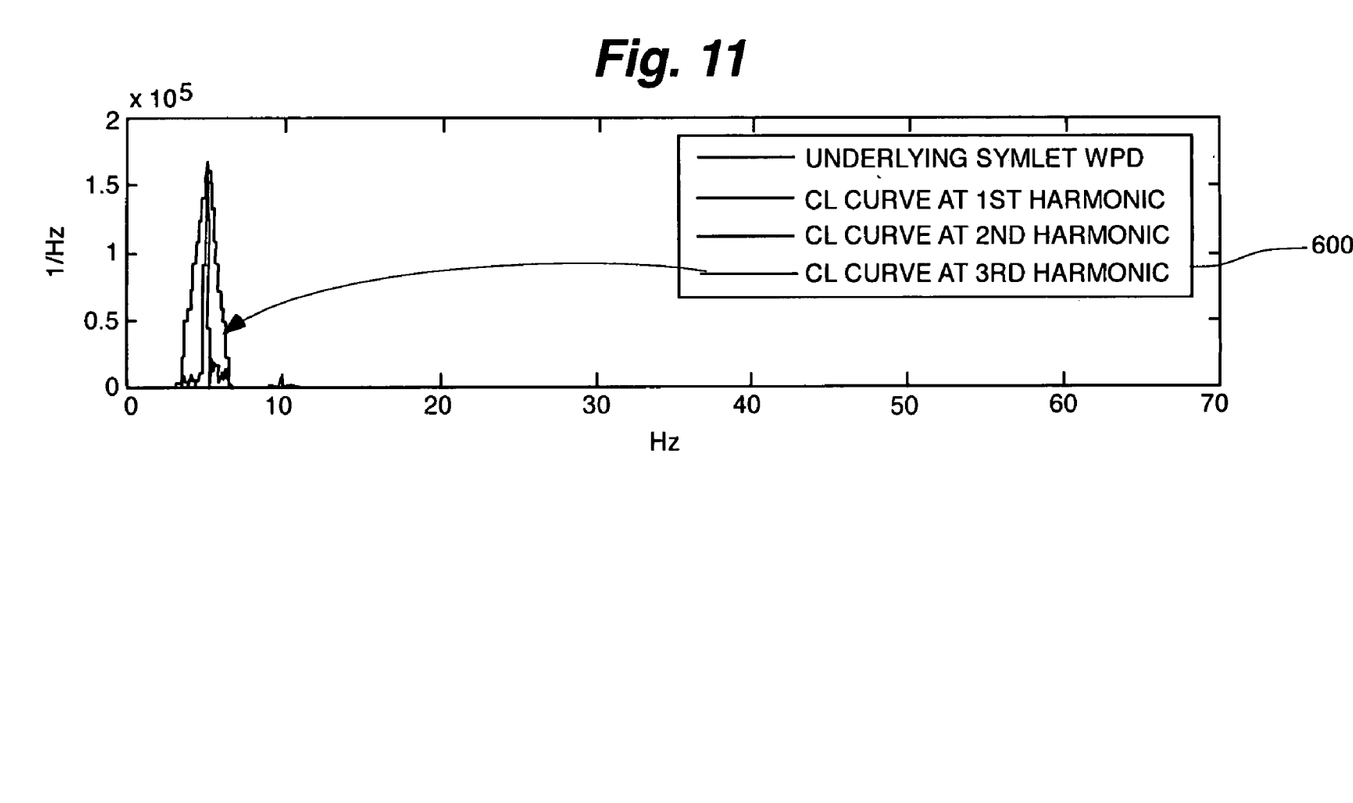
FIG. 11 is a pictorial representation of the Cauchy-Lorentz curve fitting the first three harmonics of the Symlet wavelet packet decomposition calculation.
Figure 12:
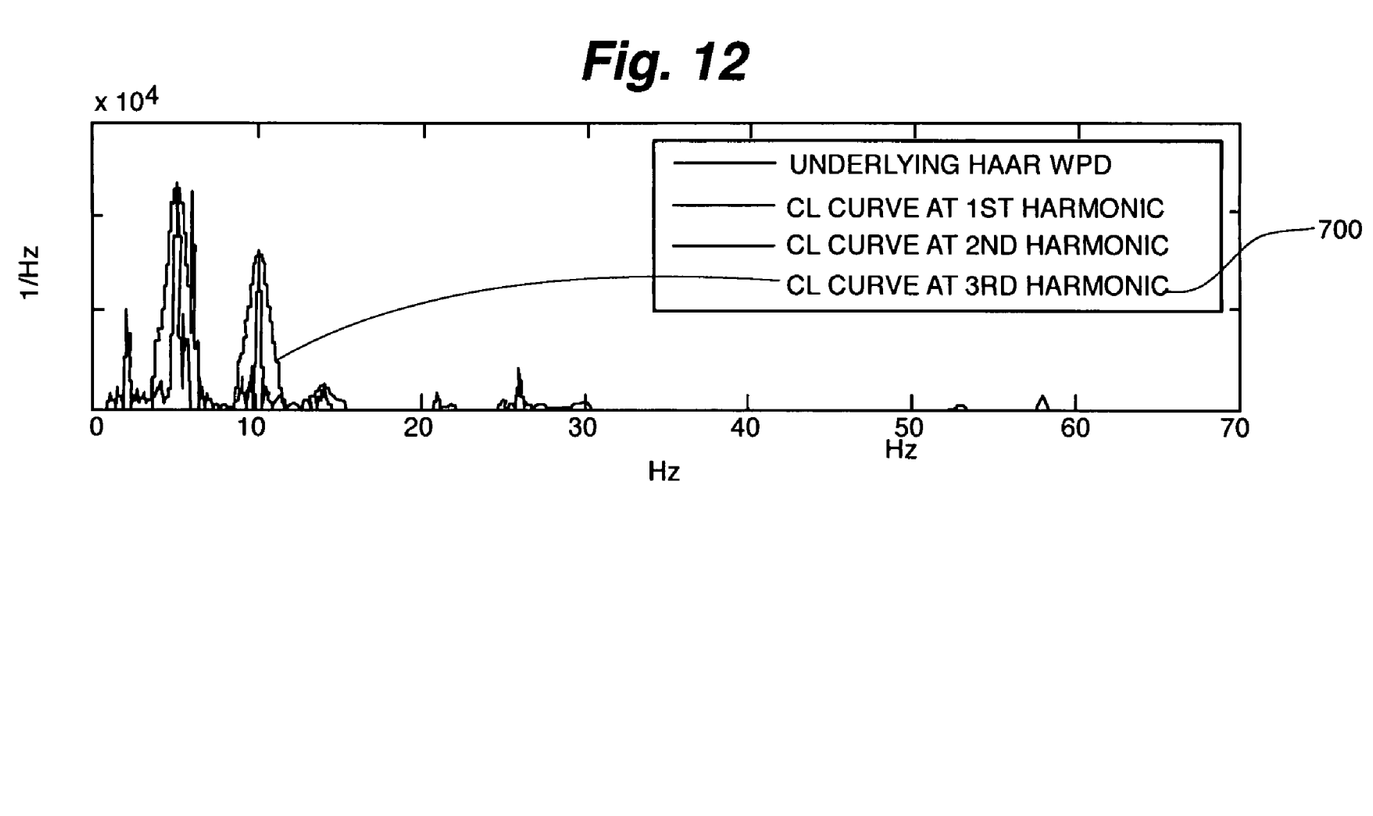
FIG. 12 is a pictorial representation of the Cauchy-Lorentz curve fitting the first three harmonics of the Haar wavelet packet decomposition calculation.

A representative implementation was carried out with commercially available software Matlab version 7 that is distributed by MathWorks of Natick Mass. Signal conversion was performed with a signal processing program and elements of the "Vigo" Wavelet Toolbox were also used. The software in the ICD will best mimic the MatLab implemented processes wherein a 2-second segment of far-field date (256 data points) was analyzed for each event. A trend line was estimated using a 4° polynomial and was subtracted from the raw signal to correct for signal drift. A power spectral density (PSD) was calculated using a Welch periodogram with Hamming window. The fundamental frequency was located between 3.5-7.5 Hz. Wavelet packet decomposition (WPD) was performed on the same data using Haar 2 tap, Daubechies 4 tap, and Symlet 20 tap wavelets. Each of these techniques differ in computational overhead but each appears to be useful for carrying out the invention. In general the applicant prefers the technique that has the least computational requirements to conserve power. Cauchy-Lorentz curves were used to estimate the first 3 harmonics. FIG. 10 at curve 500 shows the envelope of the first three harmonics using Daubechies wavelet decomposition. FIG. 11 shows the envelope of the first three harmonics using Symlet wavelet decomposition at curve 600. FIG. 12 shows the envelope of the first three harmonics using Haar wavelet decomposition at curve 700. An Energy Ratio (ER) (or Power Ratio) was calculated using the ratio of energy under the first 3 harmonics to the entire spectrum as displayed in Tables of FIG. 14 and FIG. 15. A Root Mean Square Ratio (RMSR) was calculated using a ratio of the Root Mean Square of the first 3 harmonics to the entire spectrum. Both of these measures are useful for separating arrhythmia signals form noise and artifacts. Although this exemplary technique can be used to carry out the invention, other implementations using other mathematical descriptors are possible without departing from the scope of the claims.

The applicant has found that ventricular fibrillation has a distinct signature or fingerprint associated with the arrhythmia. The calculation and determination is made and if the acquired signal is physiologic and the process meets the time domain criteria, then process 230 delivers the appropriate therapy. Likewise, if a signal is thought to be a tachyarrhythmia in the time domain, but signal analysis in the frequency domain using descriptions such as power ratio, root mean square ratio, or Shannon entropy show it to be consistent with artifact, brady-therapy will not be withheld, but rather it will continue to be delivered by process 206.

In summary the ICD relies on time domain processing of EMG signals to perform bradycardia pacing and to invoke a defibrillation treatment. However before a defibrillation treatment is delivered the ICD performs a spectral fingerprint analysis of the input waveforms. If the spectral fingerprint is a Vtreatable VT or VF episode the ICD goes ahead and delivers the defibrillation therapy. If the spectral finger prints belong to a supraventricular tachycardia or other noise artifact then the ICD does not defibrillate the heart but rather reverts to a safe pacing mode which may be asynchronous pacing at a base rate or a totally inhibited VVI standby mode.

The spectral finger print analysis for VF takes place on a short segment of acquired waveforms. Usually about two seconds worth of data. next a frequency domain analysis is performed and the energy or power present in a signature spectra are summed and compared with baseline data free of events. Several methods are taught to estimate the waveform using wavelet techniques and others. and several spectra peaks are summed. Usually the first three based on a maximum detected in a passband. The typical passband for VF is 3.5 to 7.5 hertz although variation can be expected in the optimal range. In some instances the number of harmonics can be increase up to five or more and good though not optimal detection may occur with fewer spectra peaks. The detection of VT is similar but not identical. as set forth above the passband is likely lower for optimal detection. As set forth above the detection of supraventricular tachycardia or other atrial arrhythmias it has been found that Shannon entropy metrics rather than power ratio are preferred to declare an AST or AF event.

In this fashion, the device determines the signals present upon the sensing leads to determine whether or not they are the physiologic origin based upon the spectral fingerprints analysis. If the signals are suspect, the device interrupts normal operation and reverts to a safe mode.

What is claimed is:

1. An implantable medical device of the type having a sense amplifier for detection of cardiac events on a lead system; the improvement comprising the method of:
   collecting electromyographic signals from said lead system;
   transforming the signal to the frequency domain;
   finding a frequency in a predefined pass band that is associated with ventricular arrhythmia defining a first harmonic;
   measuring the power associated with the first harmonic and the next two harmonics;
   declaring a ventricular arrhythmia if the power of the harmonics exceeds a baseline level;
   invoking a therapy if a ventricular arrhythmia is declared.

2. An implantable medical device of the type having a sense amplifier for detection of cardiac events on a lead system; the improvement comprising the method of:
   collecting electromyographic signals from said lead system;
   transforming the signal to the frequency domain;
   finding a frequency in a predefined pass band that is associated with ventricular arrhythmia defining a first harmonic;
   measuring the power associated with the first harmonic and the next two harmonics;
   declaring a ventricular arrhythmia if the power of the harmonics exceeds a baseline level and declaring that a ventricular arrhythmia is not present if the power is below the baseline level;
   canceling an otherwise scheduled therapy if a ventricular arrhythmia is not declared.

3. An implantable medical device of the type having a sense amplifier for detection of cardiac events on a lead system; the improvement comprising the method of:
   collecting electromyographic signals from said lead system;
   transforming the signal to the frequency domain;
   finding a frequency in a predefined pass band that is associated with ventricular arrhythmia defining a first harmonic;
   measuring the entropy associated with the first harmonic and the next two harmonics forming an entropy measurement;
   declaring a ventricular arrhythmia if the entropy measurement of the harmonics exceeds a baseline level;
   invoking a therapy if a supraventricular arrhythmia is declared.

4. An implantable medical device of the type having a sense amplifier for detection of cardiac events on a lead system; the improvement comprising the method of:
   collecting electromyographic signals from said lead system;
   transforming the signal to the frequency domain;
   finding a frequency in a predefined pass band that is associated with ventricular arrhythmia defining a first harmonic;
   measuring the power associated with the first harmonic and the next two harmonics;
   declaring a supraventricular arrhythmia if the entropy of the harmonics exceeds a baseline level and declaring that a supraventricular arrhythmia is not present if the power is below the baseline level;
   selecting a therapy based upon the presence or absence of the presence of the supraventricular arrhythmia.

5. An improved implantable medical device of the type having a sense amplifier for detection of cardiac events on a lead system, and having a shocking circuit to deliver a defibrillation or cardioversion shock on said lead system in the event of a detected bout of ventricular tachycardia above a time domain rate threshold; the improvement comprising the method of:
   collecting electromyographic signals from said lead system; transforming the signal to the frequency domain; finding a frequency in a predefined pass band extending from about 3.5 hertz to about 7.5 hertz that is associated with ventricular arrhythmia defining a first harmonic;
   measuring the power associated with the first harmonic and the next two harmonics;
   declaring a ventricular arrhythmia if the power of the harmonics exceeds a baseline level;

invoking a therapy if a ventricular arrhythmia is declared based upon both the power spectra and the time domain rate threshold.

6. An improved implantable medical device of the type having a sense amplifier for detection of cardiac events on a lead system, and having a shocking circuit to deliver a defibrillation or cardioversion shock on said lead system in the event of a detected bout of ventricular tachycardia above a time domain rate threshold; the improvement comprising the method of:

collecting electromyographic signals from said lead system; transforming the signal to the frequency domain;

finding a frequency in a predefined pass band that is associated with ventricular arrhythmia defining a first harmonic;

measuring the power associated with the first harmonic and the next two harmonics;

declaring a ventricular arrhythmia if the power of the harmonics exceeds a baseline level, and declaring the absence of a ventricular arrhythmia if the power spectra density is below said baseline level;

canceling a shock therapy if a ventricular arrhythmia is declared based upon the time domain rate threshold and not confirmed based upon the power of the harmonics.

7. The device of claim 6 wherein said collecting step includes:

filtering the electromyographic signals with a filter acquiring signals from about 3.5 hertz to about 7.5 hertz averaging the electromyographic signals for approximately two seconds and forming a trend line to remove baseline drift in the signal.

8. The device of claim 6 wherein said measuring step includes:

estimating the magnitudes of the first harmonic and the next two harmonics using a Haar wavelet transformation on electromyographic data transformed using wavelet packets.

9. The device of claim 6 wherein said measuring step includes estimating the magnitudes of the first harmonic and the next two harmonics using a Symlet wavelet transformation on electromyographic data transformed using wavelet packets.

10. The device of claim 6 wherein said measuring step includes estimating the magnitudes of the first harmonic and the next two harmonics using a Daubechies wavelet transformation on electromyographic data transformed using wavelet packets.

11. An improved implantable medical device of the type having a sense amplifier for detection of cardiac events on a lead system, and having a shocking circuit to deliver a defibrillation or cardioversion shock on said lead system in the event of a detected bout of ventricular tachycardia above a time domain rate threshold; the improvement comprising the method of:

collecting electromyographic signals from said lead system; transforming the signal to the frequency domain;

finding a frequency in a predefined pass band that is associated with ventricular arrhythmia defining a first harmonic;

measuring the power associated with the first harmonic and the next two harmonics;

declaring a ventricular arrhythmia if the power of the harmonics exceeds a baseline level;

computing a spectral fingerprint for the collected signals and classing the signature as VT, VF, SVT, AF or EMI;

selecting a therapy based upon the signature.

\* \* \* \* \*